United States Patent [19]

Schalkowsky et al.

[11] 4,053,110

[45] Oct. 11, 1977

[54] SHOCK PRESS

[75] Inventors: Samuel Schalkowsky, Chevy Chase, Md.; Louis L. Clipp, McLean, Va.

[73] Assignee: Exotech, Incorporated, Gaithersburg, Md.

[21] Appl. No.: 672,713

[22] Filed: Apr. 1, 1976

[51] Int. Cl.² ............................................. B02C 19/18
[52] U.S. Cl. ........................................ 241/1; 241/301
[58] Field of Search ........................... 241/1, 2, 5, 301

[56] References Cited

U.S. PATENT DOCUMENTS

| | | | |
|---|---|---|---|
| 3,165,266 | 1/1965 | Blum et al. | 241/1 |
| 3,309,032 | 3/1967 | Filz et al. | 241/1 |
| 3,458,139 | 7/1969 | Edebo | 241/1 |
| 3,556,414 | 1/1971 | Eberly, Jr. | 241/2 |
| 3,658,268 | 4/1972 | Martin | 241/301 |
| 3,887,144 | 6/1975 | Schaeffer | 241/1 |

*Primary Examiner*—Granville Y. Custer, Jr.
*Attorney, Agent, or Firm*—Morton, Sutherland & Roberts

[57] ABSTRACT

An instrument and method for applying high pressures of short duration, with very little temperature rise in the sample, to disrupt tissue, kill cells, etc., is described. The instrument uses an accelerating piston to apply a strong impact upon a sample contained in a chamber capable of holding the very high pressures produced. Following the chamber is a nozzle section. The nozzle has a receiving end cap with an impact surface and a receiver extension which can vary the distance between the nozzle exit and the impact surface. Depending upon the acceleration of the piston and sample size, a portion of the sample emerges from the nozzle as a hypervelocity jet while the remainder stays in the nozzle. The part of the sample remaining in the nozzle will have been subjected to the pressures built up by the shock wave created when the piston strikes the sample seal. The part of the sample which emerges as a jet will have been subjected to the shock pressures and, in addition, will have been subjected to high shear and decompression forces and to a jet stagnation pressure which represents the pressure exerted by the jet when it impacts the impact surface.

10 Claims, 4 Drawing Figures

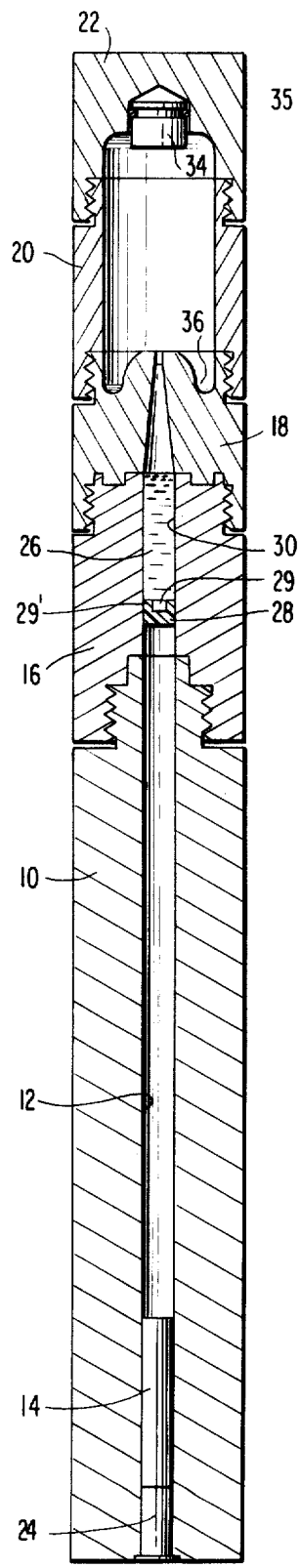
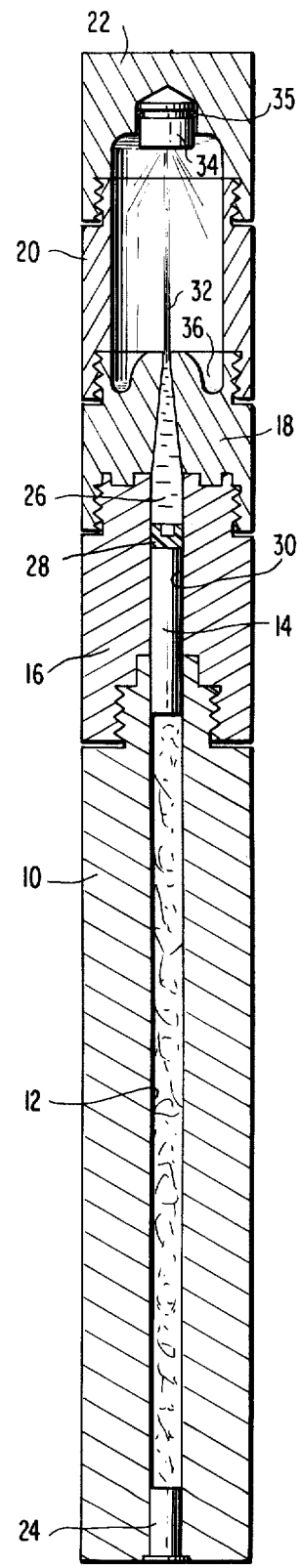
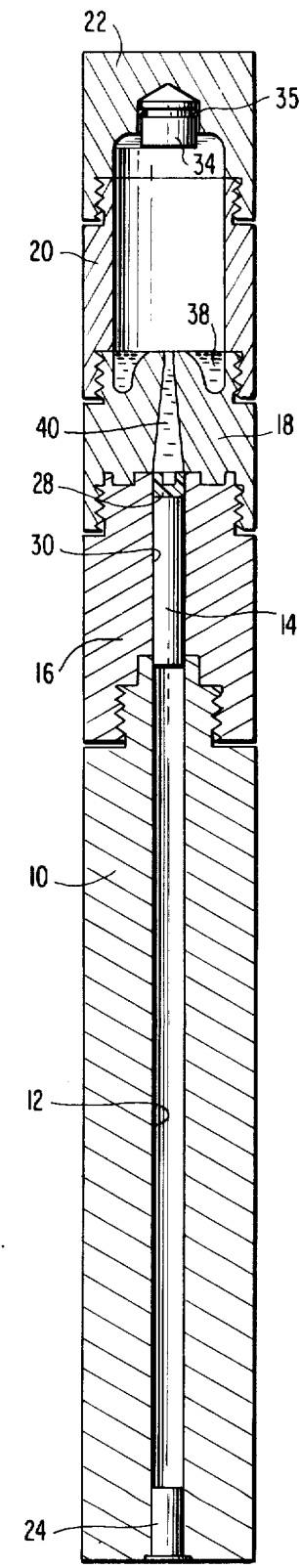
FIG. I   FIG. II   FIG. III

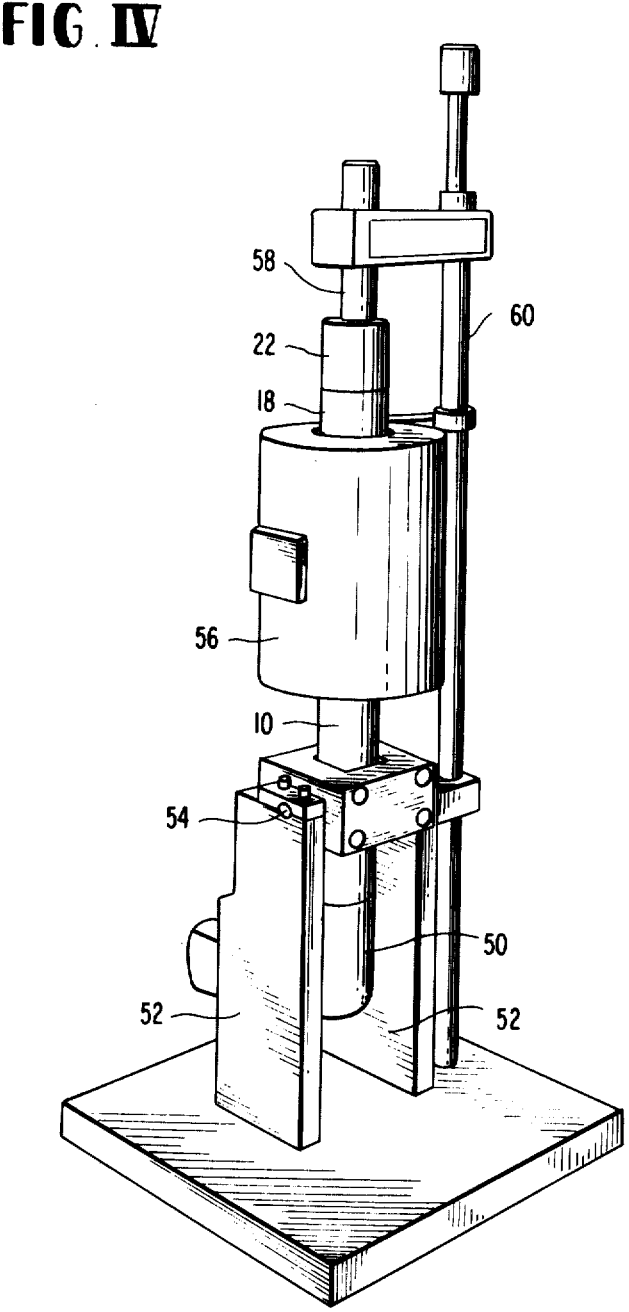
FIG. IV

SHOCK PRESS

This invention relates to an instrument and method for applying high pressures of short duration, without significant temperature rise, to disrupt tissues and kill microorganisms and cells for research purposes, to extract material from within cells, to test the effect of pressure on materials, e.g., plastics, without heat, etc.

BACKGROUND OF THE INVENTION

The use of shocks to kill cancer cells and to disrupt tissue for use in medical research is known. Two articles reporting the use of chemical explosions, such as gunpowder, are "An Explosion Instrument for Disrupting Tissues and Cells", J. A. Reyniers and M. R. Sacksteder, Journal of the National Cancer Institute, Vol. 25, No. 3, September, 1960; "Killing of Ehrlich Cancer Cells by Explosive Shocks", L. R. Maxwell et al., Oncology 24:187–192 (1970). The devices described in these articles, however, are limited in use. The devices do not have a wide range of applied pressures, control of the pressure is difficult, and recovery of the sample, particularly an uncontaminated sample, is not always easy. The instrument, and method, of this invention is superior to these devices in that it provides for a wide range of pressures which can be applied to the sample in a controlled fashion. The device also allows for easy removal of the sample while keeping differently treated portions of the sample separate. Unlike the device of Reyniers et al., the instrument of this invention permits the application of a broad range of pressures to the sample in a controlled fashion. The magnitude of the pressures and the length of time they are applied to the sample is controlled by the acceleration of the piston, the size of the sample, the nozzle, the length of the extension, etc., as more fully described below. In the device of Reyniers et al., there is no acceleration of a piston to impact the sample and create a hypervelocity jet. Accordingly, the high pressures and forces applied to the sample cannot be attained and the pressure cannot be controlled over the wide range of pressures as in the instrument of this invention.

DESCRIPTION OF THE INVENTION

For convenience, the following nomenclature will be used for the various pressure conditions described in connection with this invention. Shock-Pressures, or Chamber-Pressures will refer to the stresses applied to material which remains in the nozzle after processing. These pressures are the pressures created by the impact of the piston on the sample which sends a shock wave of high intensity and short duration through the sample. Decompression-Impact will refer to the stresses applied to material which emerges from the nozzle as a hypervelocity jet but is allowed to decompress over the receiver extension distance before impact on the end cap. Maximum Impact is decompression-impact pressure where the receiver extension is not used and the sample is subjected to maximum impact pressure. The stagnation pressure represents the pressure exerted by the jet if it were to impact a hard surface within a preselected distance from the nozzle exit. Several options are provided for utilization of the stagnation pressure. If only the receiver cap is used, omitting the receiver extension, the sample is subjected to the full stagnation pressure impact, as the impact surface is, in this case, close to the nozzle exit. If the receiver extension is used, the jet velocity decreases rapidly as it travels through the receiver. In the latter case, the material in the jet will have been exposed to the pressure due to velocity build-up and to the extensive forces of decompression in the receiver extension; however, the impact pressure, when the jet finally strikes the impact surface, is substantially reduced.

The receiver end cap configuration of the instrument allows separate removal of the sample which was subjected to impact pressures, without mixing it with the portion of the sample that may have remained in the nozzle. The proportions of these two sample categories are controllable by the choice of initial sample volume and acceleration force applied to the sample.

The instrument consists of two main sections: an actuator and a pressure chamber. The pressure chamber comprises a barrel having a bore through which a free-floating piston is accelerated by the actuator, the piston, a sample holder, a nozzle, a receiver extension and an end cap. The nozzle has a trough surrounding the nozzle exit for collecting the processed sample. Each of these sections is separable and designed for easy cleaning. Positioning of a seal to hold the sample in the sample holder determines sample capacity.

The actuator initiates the pressure sequence by accelerating the piston through the barrel to strike the seal and sample. This produces a shock wave which is propagated through the sample and initiates a high velocity jet through the nozzle. The jet rapidly decompresses as it travels through the receiver and the sample then impacts the end cap. Depending on the length of the receiver extension and acceleration of the piston, an impact pressure of up to 250,000 psi can be applied to the sample, in addition to the shock-pressures previously exerted at impact of the piston on the sample which can be on the order of 150,000 psi.

Upon completion of the cycle, the piston will have forced most of the sample through the nozzle into the collection trough. Removal of the receiver extension permits immediate access to the processed sample in the trough and facilitates separate removal of the sample remaining in the nozzle. A gun firing blank cartridges provides a convenient actuator, since there is commercially available a wide-range of blank cartridges having different powder loadings, although gas or hydraulic actuator can be used.

The instrument of this invention is further illustrated in the attached drawings wherein:

FIG. I, II and III are schematic illustrations of the instrument showing the instrument in its loaded, fired and finished stages of a complete cycle of operation.

FIG. IV is a plan view of the complete instrument.

As illustrated in FIGS. I, II and III, the pressure chamber of the instrument comprises barrel 10 having bore 12, piston 14 in bore 12, sample holder 16, nozzle 18, receiver extension 20 and end cap 22. A cartridge 24 in barrel 10 is used to propel piston 14 down bore 12 to strike the sample. The sample 26 is held in the sample holder 16 by a seal 28. Frozen samples and gells can be used in which case the seal may be unnecessary. The barrel, sample holder, nozzle, receiver extension and end cap are each separable and preferably made of non-corrosive, surgical steel which can be autoclaved or dry-heat sterilized. The capacity of the instrument is determined by the size of the bore 30 in holder 16. A convenient manner of handling different sample sizes is to size bore 30 to one dimension, e.g., 5 ml., and arrange for placement of the seal to provide for known sample sizes, i.e., in graduated amounts up to 5 ml. in this instance. Seal 28 is preferably formed of plastic or rubber with a cup-like forward end having depression 29. In this arrangement, when the seal is forced up the bore 30, the lip 29' of the cup is pressed against the wall of bore 30 to ensure that no sample escapes behind the seal.

FIG. 4 is a plan view of the instrument shown in its preferred firing position. The instrument includes actuator 50, which is a conventional blank cartridge gun, connected to barrel 10. The barrel and gun are supported by plates 52 so that they pivot about axis 54. Accordingly, the gun can be in the horizontal position for loading a cartridge. A sound muffler 56 is also provided. The seal and sample are loaded when the instrument is in the vertical position. A safety screw rod 58 is provided to hold down end cap 22 and cock actuator 50. A safety feature found in commercial guns frequently requires cocking of the gun before it can be triggered. Support rod 60 supports the screw rod 58 and muffler 56.

FIG. 1 is a schematic diagram of the major working parts, indicating the location of the piston, seal and sample before firing. Preferably, the instrument is arranged vertically so that piston 14 is fired upward. Piston 14 and cartridge 24 are first inserted in the barrel. Seal 28 is then placed in the sample holder 16. The liquid sample 26 is placed above seal 28 and the nozzle 18, extension 20 and cap 22 are screwed down.

When cartridge 24 is fired, shown in FIG. II, piston 14 accelerates through barrel 10 until it strikes seal 28. This produces a shock wave which propagates through the sample, pressurizing the sample and forcing a high-velocity jet 32 of sample material through nozzle 18. The portion of the sample in the jet decompresses as it leaves the nozzle and then impacts against the surface of impact plug 34 in the end of cap 22 and the processed sample 38 from jet 32 is collected in trough 36, as shown in FIG. III. Plug 34 is made from a very hard metal is held in place by o-ring 35.

Sample 40 which remains in nozzle 18 has been subjected only to the shock pressures, or chamber pressures created by the shock wave. When this pressure on the sample is suddenly released in the extension 20, there is an explosive effect due to shear forces and pressures of decompression so that the cells in sample portion 38 are destroyed or ruptured both upon pressurization and upon decompression, as well as impact on plug 34. The magnitude of these two pressures, and the time they are applied, i.e., the pressure history of the sample, can be varied by varied the force with which piston 14 strikes seal 28 and the volume and velocity of the jet 32. The force with which piston 14 strikes seal 28 is determined by the acceleration force applied to the piston, which can be varied by varying the energy applied to the piston, e.g., by varying the cartridge size, the length of barrel 10 and the placement of piston 14 within barrel 10. The initial acceleration force is greatest the closer the piston is to the cartridge. Shock pressures of up to about 150,000 psi can be obtained using commercially available blank cartridges as the energy source to accelerate the piston. The effect of decompression on the sample can also be varied by varying the initial shock pressure, the size and shape of the nozzle, and the length of receiver extension 20. If desired, several nozzle openings can be used. The pressure history of the sample in jet 32 is generally determined by the quantity of the sample ejected from holder 16 and the time in which it is ejected. For example, a long nozzle allows the shock pressure to rise gradually. Also, as the size of the exit opening of the nozzle increases, the pressure at which jet 32 exits decreases and as the angle of the nozzle bore decreases the greater will be the shock pressure because in this case the shock wave reflects within bore 30 and builds up the pressure faster. Also, the velocity of jet 32 will be higher the smaller the nozzle. Accordingly, the initial effect of the jet striking surface 34 will be greatest with small nozzles.

The entire operation of the instrument occurs within a few, e.g., 2 to 4, milliseconds, and typically the application of pressure to the sample lasts about a millisecond. Measurements on the sample with a few seconds, e.g., 2 to 3, after the operation is complete show less than a 3° C. rise in sample temperature during processing.

The following examples serve to further illustrate the invention.

EXAMPLE I

Aluminum calibration plates are available for determining the pressures developed by the instrument of this invention. Penetration of a calibration plate is a function of the stagnation pressure developed by the jet when it hits the plate. Table 1 gives pressures for different cartridges, and the corresponding depths of penetration, for a 2 ml. sample volume in the sample holder. The nozzle had an angle of 13°, an opening 0.1 inch in diameter, and was 1¼ inches long. The piston was a 2¼ inch teflon piston in a ⅜ inch bore. There was ¼ inch between the nozzle exit and surface 34. No extension was used for the data for Table 1. For the data of Table 1A, a 2 inch extension was used. The distance between the piston and the seal was about 2 inches. The calibration plate is placed in the bore which normally contains plug 34.

TABLE 1

PRESSURES DEVELOPED BY CARTRIDGES AND DEPTHS OF PENETRATION OF CALIBRATION PLATES

| Commercial Identification | | | Chamber Pressure, | Impact Pressure, | Penetration, |
|---|---|---|---|---|---|
| No. | Color | Caliber | psi | psi | Inches |
| 11 | Red | .38 | 150,000 | 250,000 | .25 |
| 10 | Yellow | .38 | 140,000 | 210,000 | .20 |
| 9 | Green | .38 | 125,000 | 180,000 | .15 |
| 8 | Brown | .38 | 115,000 | 150,000 | .10 |
| 8 | Brown | .22 Long | 110,000 | 140,000 | .08 |
| 7 | Gray | .22 Long | 100,000 | 110,000 | .05 |
| 6 | Purple | .22 Short | 90,000 | 90,000 | .03 |
| 5 | Red | .22 Short | 70,000 | 70,000 | .01 |
| 4 | Yellow | .22 Short | 50,000 | 50,000 | .005 |
| 3 | Green | .22 Short | 35,000 | 35,000 | mark |

TABLE 1A

| | | | | | |
|---|---|---|---|---|---|
| 11 | Red | .38 | 150,000 | 180,000 | .15 |
| 8 | Brown | .38 | 115,000 | 110,000 | .050 |
| 4 | Yellow | .22 Short | 50,000 | 35,000 | mark |

EXAMPLE II

The extent of kill of Bacillus Subtilis, var. Niger spores and other microorganisms is a means of demonstrating the effect of the instrument. The method involves plate counts of the sample prior to and after processing through the instrument.

Experiments on B. Subtilis spores show the results set forth in Table 2 using different cartridges and the instrument of Example I. B. Subtilis is a standard used to determine the extent of sterilization possible.

TABLE 2

(B. SUBTILIS SPORES — $10^6$)

| Sample | Sample Vol. | Cartridge No. | Pressure P.S.I. | % Kill (Avg. of Tests) | No. of Tests |
|---|---|---|---|---|---|
| Chamber | 4 ml. | 4 | 35K | 60.9 | 3 |
| Chamber | 2 ml. | 4 | 50K | 55.8 | 3 |
| Chamber | 2 ml. | 7 | 100K | 89.9 | 3 |
| Chamber | 2 ml. | 8 (.38) | 115K | 95.1 | 3 |
| Chamber | 2 ml. | 10 | 140K | 98.9 | 5 |

EXAMPLE III

The ubiquity and functional significance of adenosine triphosphate (ATP) in metabolism allows its assay to be an excellent monitor of the amount of biological material in a specimen.

Heretofore, the methods for removing the ATP associated with bacterial cells have involved either the use of strong reagents such as nitric acid and/or high temperatures. The present instrument provides for rapid rupturing of the cells to release the ATP, without such severe conditions, in a manner comparable with or superior to existing methods insofar as sensitivity is concerned. Table 3 sets forth calibration data using this instrument to recover ATP and Table 4 presents the data for the amount of ATP extracted from E. Coli cells with a 2 ml. sample, the nozzle of Example I, a 2 inch receiver extension, and a No. 11 cartridge.

TABLE 3

| ATP $\mu g/ml$ Initial | Light Units |
|---|---|
| Blank | $1.52 \times 10^5$ |
| $10^0$ | — |
| $10^{-1}$ | $1.91 \times 10^9$ |
| $10^{-2}$ | $1.86 \times 10^8$ |
| $10^{-3}$ | $1.67 \times 10^7$ |
| $5 \times 10^{-4}$ | — |
| $1 \times 10^{-4}$ | $1.66 \times 10^6$ |
| $5 \times 10^{-5}$ | $7.41 \times 10^5$ |
| $1 \times 10^{-5}$ | $1.80 \times 10^5$ |
| $5 \times 10^{-6}$ | $0.74 \times 10^5$ |
| $1 \times 10^{-6}$ | $0.11 \times 10^5$ |
| $5 \times 10^{-7}$ | 0.00 |

TABLE 4

| No. of Cells in Dilution per ml | Light Units | $\mu g$ ATP per ml |
|---|---|---|
| $6.06 \times 10^8$ | — | — |
| $6.06 \times 10^7$ | $5.75 \times 10^8$ | $3.23 \times 10^{-2}$ |
| $6.06 \times 10^6$ | $2.27 \times 10^7$ | $1.28 \times 10^{-3}$ |
| $6.06 \times 10^5$ | $1.78 \times 10^6$ | $1.00 \times 10^{-4}$ |
| $3.03 \times 10^5$ | — | — |
| $6.06 \times 10^4$ | $3.02 \times 10^5$ | $1.70 \times 10^{-5}$ |
| $3.03 \times 10^4$ | $2.08 \times 10^5$ | $1.17 \times 10^{-5}$ |
| $6.06 \times 10^3$ | $0.67 \times 10^5$ | $3.76 \times 10^{-6}$ |
| $3.03 \times 10^3$ | $0.61 \times 10^5$ | $2.87 \times 10^{-6}$ |
| $6.06 \times 10^2$ | $0.20 \times 10^5$ | $1.12 \times 10^{-6}$ |

EXAMPLE IV 1.8 ml. samples containing 8.4 times $10^{10}$ viable M. Luteus ATCC 4698 cells in RT-buffer were processed in the instrument under the following four conditions:

| TEST | POWDER LOAD | PRESSURE |
|---|---|---|
| 1 | No. 11 | Maximum Impact |
| 2 | No. 11 | Decompression-Impact |
| 3 | No. 7 | Maximum Impact |
| 4 | No. 7 | Decompression-Impact |

Test 2 and 4 included use of a 4 inch extension. Otherwise, the instrument of Example I was used. A mix of the processed sample, containing both the residual material in the nozzle and the impacted material, were assayed for protein contents of the supernates by the method of Lowry, Rosenbrough, Farr and Randall, J. Biol. Chem. 193, 265, (1951), using bovine albumin as standard.

It was found that protein yields in the above assays were essentially equivalent to those obtained from the same cell densities by a four minute sonication (7 amp) of 7-10 ml.

Protein from each sample described above was diluted to about 250 $\mu g/0.05$ ml. in RT-buffer and duplicate samples were electrophoresed on 7% polyacrylamide gels at a constant current of 3 mA/gel. As a control, duplicate samples of extract prepared by sonication from M. Luteus was included for which a standardized electrophoretic protein profile has been established (Fox, Microbias, In Press, 1975). One of each gel was stained with amido black for total protein and the duplicate gels were assayed for catalase activities according to the method of Gregory and Fridovich, Anal. Biochem. 58, 57, (1974).

It was noted that the protein obtained from the differently shocked samples have some qualitative band differences when compared to the protein profile from the sonication control. The differences tend to be localized mostly in the low mobility region of the gels and near the top of the gels. This is particularly evident for protein obtained from the highest load samples and less so for protein derived from the intermediate load stresses. The enzyme catalase was detected qualitatively from each of the stressed samples. The achromatic activity bands were noted to have electrophoretic mobilities essentially identical to the catalase band of the sonicated control.

EXAMPLE V

The temperature rise during operation of the instrument was measured using a No. 11 cartridge and the instrument of Example I with 2 and 5 ml. samples of water. The temperature recorded was taken in trough 36.

The results are set forth in Table 5.

TABLE 5

| Test | Sample Size (ml.) | Temperature Before | (° C.) After |
|---|---|---|---|
| 1 | 5 | 24.6 | 27.4 |
| 2 | 2 | 24.2 | 26.5 |
| 3 | 5 | 25.8 | 27.6 |

The temperature of the mist in the extension from a 2 ml. sample using a 2 inch extension was measured immediately after a cycle. The initial temperature was 22° C. and the temperature of the mist was 23.5.

EXAMPLE VI

The effect of varying the nozzle exit opening upon the kill of B. Subtilis var. Niger spores was demonstrated. The instrument used was like that of Example I except for the size of the nozzle opening. A No. 11 cartridge was used.

| Nozzle Exit (In.) | Kill (%) |
|---|---|
| 0.081 | 82 - 90 |
| 0.089 | 86 - 90 |
| 0.100 | 93 - 94 |

It is claimed:

1. An instrument for applying controlled high pressures to a sample with little temperature rise in the sample comprising barrel means containing a bore, a free-moving piston arranged in said bore, said bore forming an acceleration path for said piston, sample holding means attached to one end of said barrel and having a sample holding bore adapted to contain said sample aligned with said bore in the barrel and forming a part of the piston acceleration path such that said piston can strike the sample at one end of its travel along said acceleration path, nozzle means attached to said sample holding means and having a nozzle connected with said sample holding bore, end cap means spaced from the exit of said nozzle and forming a chamber at the exit of said nozzle, means for accelerating said piston along said acceleration path to strike the sample and create a shock wave in said sample to force a portion of the sample through the nozzle as a high velocity jet into said chamber, and collecting means for collecting said portion of the sample in said chamber.

2. The instrument of claim 1 wherein the sample holding means includes a seal adjustably positioned in said sample holding bore to accommodate a varying size of the sample.

3. The instrument of claim 1 wherein the end cap means includes impact surface means aligned with said nozzle, said jet striking said impact surface means.

4. The instrument of claim 1 wherein the collecting means is a trough in said nozzle means surrounding the exit of said nozzle.

5. The instrument of claim 1 wherein the means for accelerating said piston is a blank cartridge gun.

6. A method for applying a controlled pressure history to a sample including high pressures and very little temperature increase comprising placing said sample in a chamber having a nozzle as the only exit; accelerating a piston along a path to strike said sample; striking said sample and force a portion of the sample through the nozzle as a high velocity jet; the portion of said sample remaining in the chamber being subjected to an impact pressure the history of which is controlled by predetermining the acceleration of the piston, the volume of the jet and the rapidity with which the jet exits from the nozzle; said portion of the sample forming the jet being subjected to said impact forces and to the forces of decompression exiting from said nozzle.

7. A method as defined in claim 6 wherein the jet strikes an impact surface, thereby subjecting the portion of the sample forming the jet to an impact pressure controlled by selecting the velocity of the jet upon impact.

8. The method of claim 6 further including separately collecting the portion of the sample forming the jet and the portion of the sample remaining in the nozzle.

9. The method of claim 6 wherein said sample is formed of microorganisms that are killed without the use of heat.

10. The method of claim 6 wherein the sample is formed of cells that are ruptured without the use of heat.

* * * * *